(12) United States Patent
Chodorow et al.

(10) Patent No.: US 6,530,919 B1
(45) Date of Patent: Mar. 11, 2003

(54) INFRARED COAGULATOR WITH DISPOSABLE TIP LIGHT GUIDE

(75) Inventors: Ingram S. Chodorow, Santa Fe, CA (US); Kerry Blair, Overland Park, KS (US); Scott Marlow, Chesterland, OH (US)

(73) Assignee: Redfield, Inc., Rochelle Park, NJ (US)

( * ) Notice: Subject to any disclaimer, the term of this patent is extended or adjusted under 35 U.S.C. 154(b) by 0 days.

(21) Appl. No.: 09/430,460

(22) Filed: Oct. 29, 1999

Related U.S. Application Data

(60) Provisional application No. 60/106,401, filed on Oct. 30, 1998.

(51) Int. Cl.[7] .............................................. A61B 18/18
(52) U.S. Cl. ........................... 606/13; 606/10; 606/11; 606/28; 606/41; 607/88; 607/96; 607/100
(58) Field of Search .............................. 607/88, 89, 96, 607/100; 606/7–9, 10–15, 41, 42, 49, 27, 28

(56) References Cited

U.S. PATENT DOCUMENTS

| | | | | |
|---|---|---|---|---|
| 4,227,535 A | * | 10/1980 | Connor | 128/401 |
| 4,233,493 A | | 11/1980 | Nath | |
| 4,539,987 A | | 9/1985 | Nath et al. | |
| 4,693,244 A | | 9/1987 | Daikuzono | |
| 4,865,029 A | | 9/1989 | Pankratov et al. | |
| 4,994,059 A | * | 2/1991 | Kosa et al. | 606/12 |
| 5,298,026 A | * | 3/1994 | Chang | 606/15 |
| 5,408,482 A | * | 4/1995 | Nagano et al. | 372/31 |
| 5,409,479 A | * | 4/1995 | Dew et al. | 606/9 |
| 5,643,253 A | | 7/1997 | Baxter et al. | |
| 5,662,643 A | * | 9/1997 | Kung et al. | 606/3 |
| 5,755,752 A | | 5/1998 | Segal | |
| 6,135,997 A | * | 10/2000 | Laufer et al. | 606/27 |
| 6,139,527 A | * | 10/2000 | Laufer et al. | 604/114 |
| 6,273,886 B1 | * | 8/2001 | Edwards et al. | 606/34 |
| 6,325,789 B1 | * | 12/2001 | Edwards et al. | 606/41 |

OTHER PUBLICATIONS

1988 Redfield Corporation New and Improved for the '90's The Non–Surgical, Non–invasive Infrared Coagulator (IRC) brochure.*

* cited by examiner

*Primary Examiner*—Linda C. M. Dvorak
*Assistant Examiner*—Ahmed Farah
(74) *Attorney, Agent, or Firm*—Amster, Rothstein and Ebenstein

(57) ABSTRACT

An apparatus for applying light radiation to an object include: a source of light radiation including infrared radiation, a light guide having a proximal end optically coupled to the source of light radiation and a distal end with a light radiation emitting end surface, a power supply which supplies power to the light radiation source, a photo light energy detector disposed within the apparatus so as to receive energy output emitted from the light radiation source, the photo light energy detector producing an output in response to the received energy output; and a controller coupled to the photo light energy detector and the light radiation source; wherein the controller receives the output from the photo light energy detector and controls the source of light radiation to produce a predetermined light radiation intensity in response to the output.

20 Claims, 17 Drawing Sheets

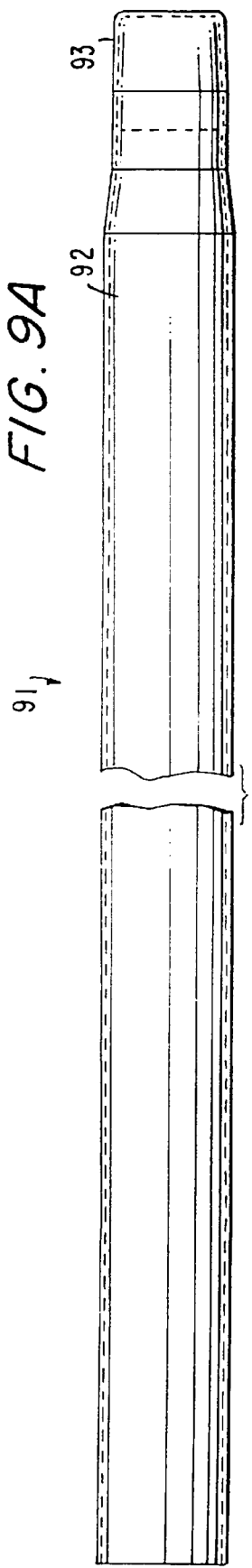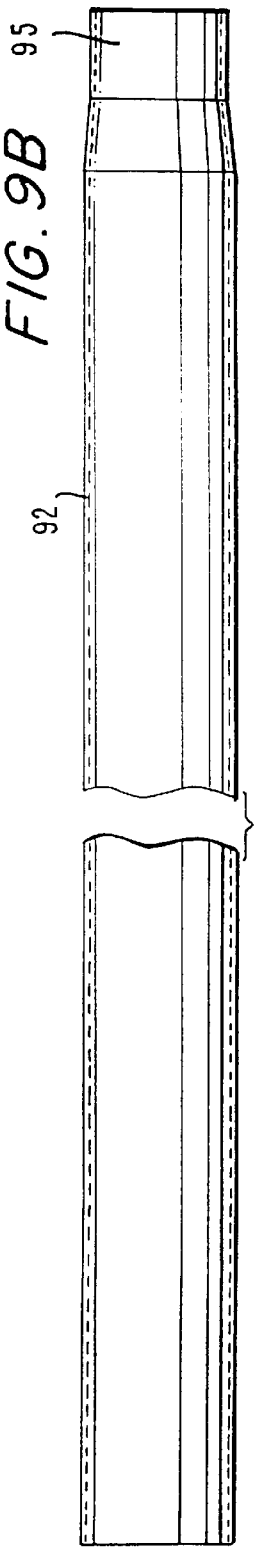

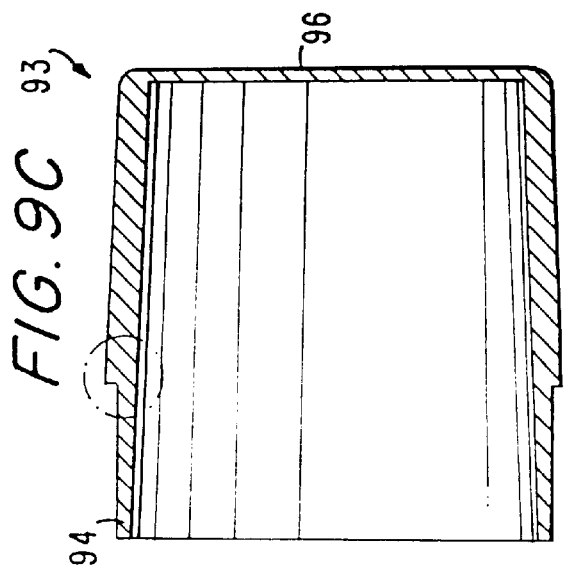
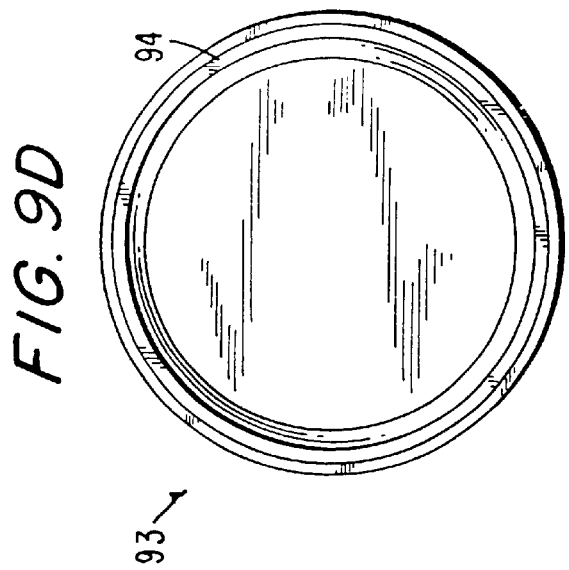
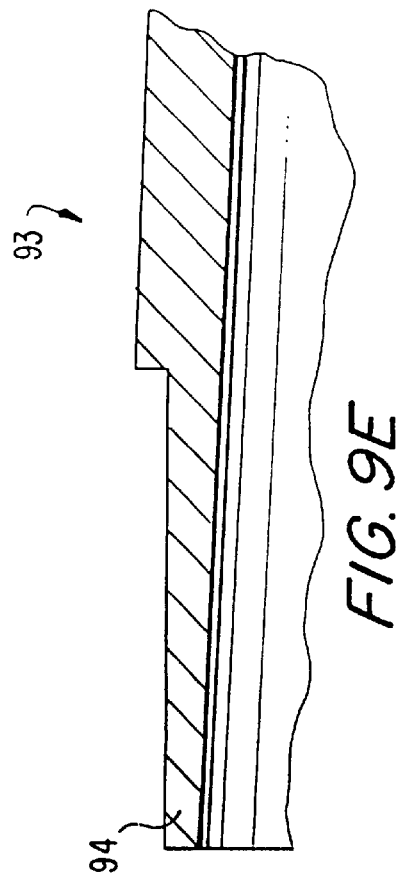

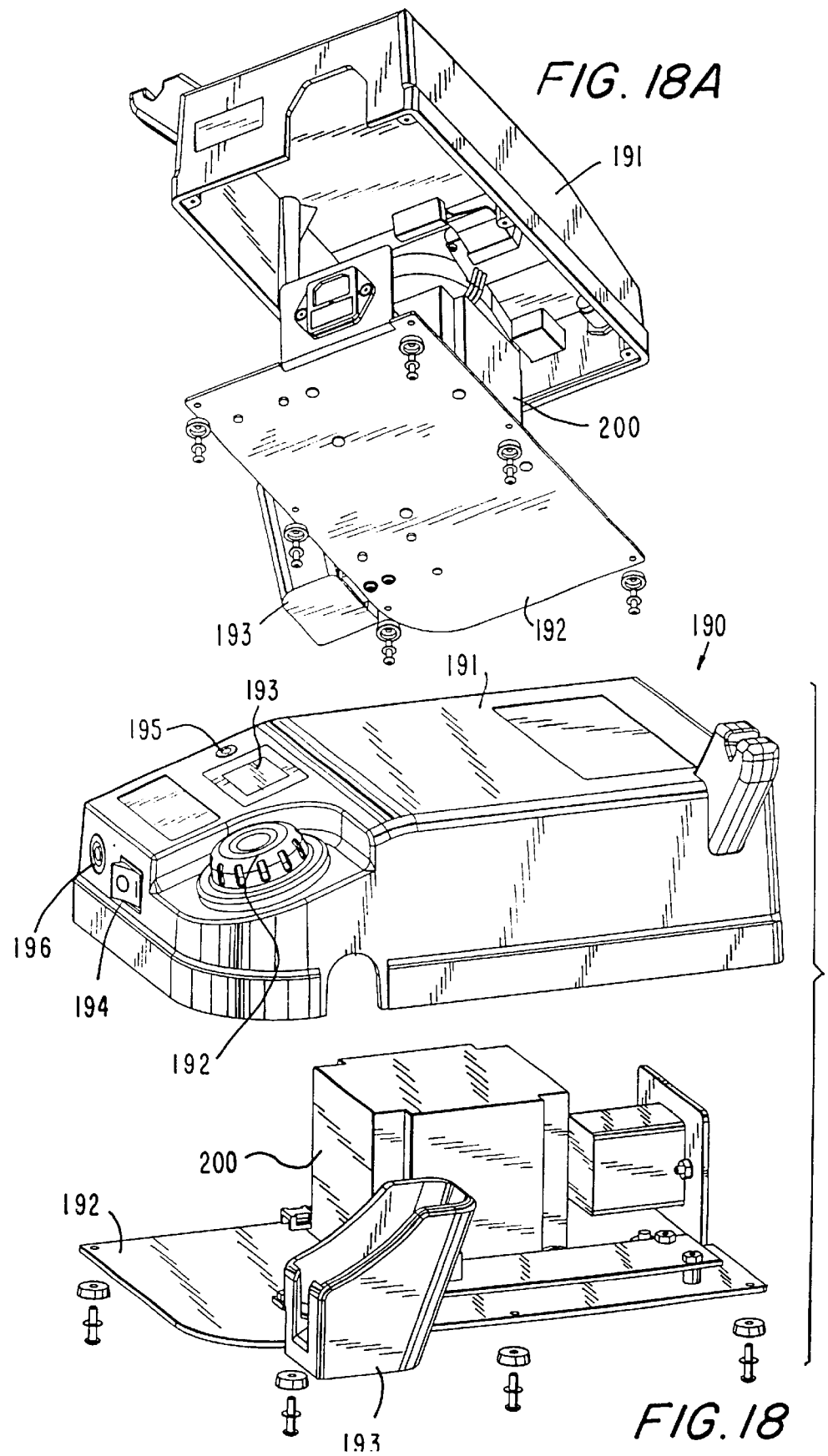

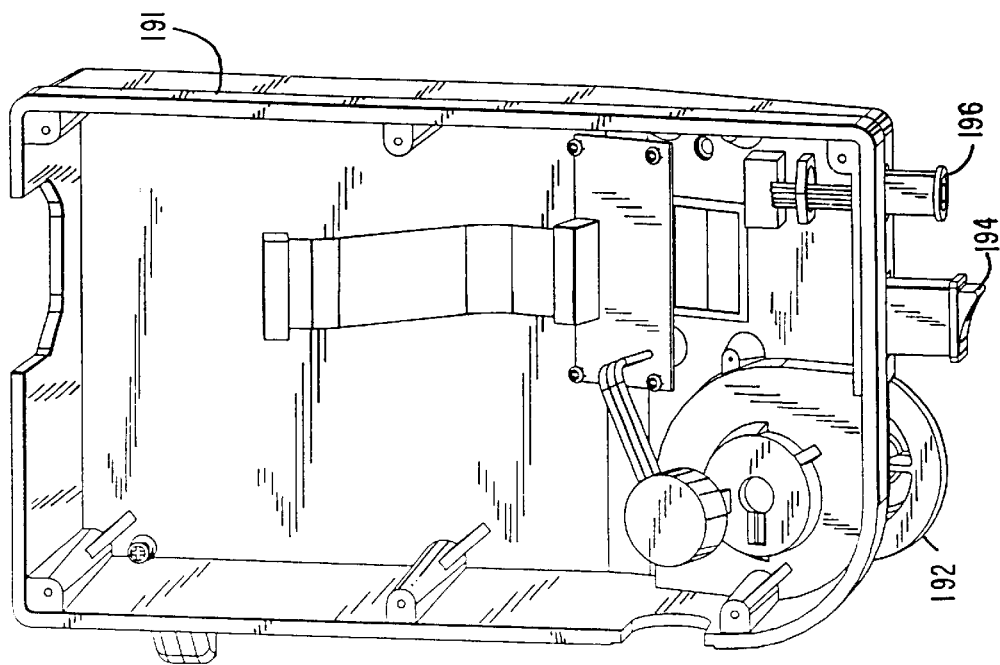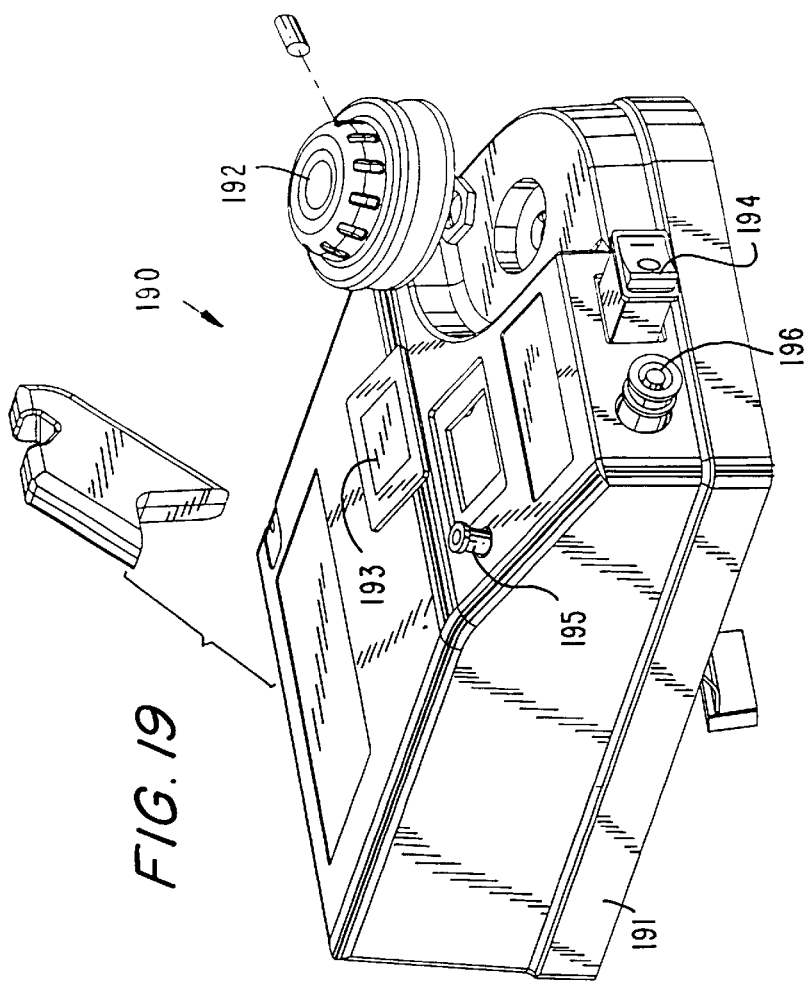

INFRARED COAGULATOR WITH DISPOSABLE TIP LIGHT GUIDE

CROSS REFERENCE TO RELATED APPLICATION

This application is based on and claims priority to United States Provisional Patent Application No. 60/106,401 filed Oct. 30, 1998, entitled INFRARED COAGULATOR WITH DISPOSABLE TIP LIGHT GUIDE.

BACKGROUND OF THE INVENTION

The present invention relates to an apparatus for causing thermal coagulation and, more particularly, relates to an apparatus for applying intense light radiation to a limited area of tissue for causing thermal coagulation that results in tissue necrosis.

Various medical procedures require an apparatus to cause hemorrhoid shrinkage or cause coagulation at a site of bleeding. For example, coagulation may be induced at the site of a bleeding hemorrhoid or at a site of hemorrhaging at a bleeding blood vessel stump. Known coagulation systems, for example, use high frequency electric currents to cause coagulation. These systems, however, use the human body as an electrical conductor and thus require external grounding using a grounding pad. Further, such electrosurgical devices do not readily induce coagulation in a controllable and reproducible manner, and thus the depth of necrosis cannot be precisely controlled. Additionally, the metallic probes used tend to adhere to the tissue, thereby impeding homeostasis.

Alternatively, thermal coagulation is induced by exposure to a laser beam or an infrared light source. Though both sources have advantages over electrocoagulation, the infrared light sources are preferred because the light source is cheaper than and-YAG laser or other laser sources.

Known infrared light source thermal coagulation systems typically include a probe with a light radiation source enclosed in a housing. The source emits light radiation through a light exit surface for transmission along a light guide. The light guide is a light transmissive material which delivers the light radiation to the tissue surface and heats the surface. Examples of known apparatus for causing thermal coagulation using a light source are described in U.S. Pat. No. 4,233,493, issued Nov. 11, 1980, and U.S. Pat. No. 4,539,987, issued Sep. 10, 1985, the disclosures of which are incorporated herein by reference, and by Redfield Corporation Brochure Ĉ 1988 attached hereto as Appendix A.

In the known systems, however, the light guide is typically a straight rod or slightly bent and is thus often difficult to apply specific to the desired tissue region to be treated.

Further, the intensity of the emitted light cannot be precisely controlled and thus the coagulation is also not readily controlled. Another disadvantage is that the probe must be sterilized each time prior to its use.

It is therefore desirable to have an infrared coagulation device which overcomes the above-mentioned problems.

SUMMARY OF THE INVENTION

The present invention provides an infrared coagulation apparatus in which light is transmitted along a light guide having a bend that changes the direction of the light at a greater angle than in known systems, in which the intensity of the infrared light source is controlled by a feedback loop and which includes a disposable tip at the end of the light guide.

The infrared coagulation apparatus of this invention includes a non-coherent, multispectral light source having a spectral maximum of about 10,000 angstroms. A portion of the visible light spectrum is also emitted to ascertain operation of the lamp. The light emitted from the lamp is transmitted along a light guide which may be comprised entirely of quartz or which may include other light transmissive materials, such as sapphire, with a quartz portion located at the distal end. Advantageously, the distal end of the light guide includes a bend that causes the light to exit at angles up to an angle substantially perpendicular to the axis of the light guide and thus permits the probe to more easily contact the tissue area. A reflective coating surrounds the cylindrical walls of the light guide to further promote transmission of the light radiation along the path of the light guide as well as around the bend. A cladding layer, such as neoprene, surrounds the reflective coating to protect the coating, and an additional support cladding typically surrounds the neoprene cladding. A metal end cap is secured around the light guide near the distal end.

Alternatively, a straight quartz rod serves as the light guide and is covered with the reflective coating along the walls and at the distal end. A portion of the wall near the distal end is left uncoated so that the light reflects off the coating and exits at an angle substantially perpendicular to the axis of the rod.

Further, in accordance with this invention, a disposable contact tip covers the distal end of the light guide. The disposable tip includes a plastic cap that is secured onto the metal end cap and a Teflon or PVC plate optical window that covers the polished end surface of the light guide.

Alternatively, the disposable tip and sheath includes a plastic cylindrical body having a Teflon or PVC optical window which covers the contact end of the cylindrical body. A step-down section is attached to the opposite end of the cylindrical body and is arranged to be concentric with the cylindrical body but with a smaller diameter than the cylindrical body for secure insertion into the metal end cap of the light guide. A clear plastic sheath is also attached at this end of the cylindrical body and is sealed over the step-down section and extends over the surface of the cladding. The proximal end of the sheath is attached to a retainer ring having another step-down section which is capable of sliding over a retaining collar in the cladding to secure the proximal end of the sheath to the cladding. A pull tab is provided at the proximal ring so that the sheath and end cap can be removed after use by pulling on the pull tab and tearing a weakened notch in the step-down section to permit the sheath to be torn off the cladding and prevent its reuse.

In further accordance with the,invention, a power supply and control circuit controls the operation of the infrared lamp. A microcontroller delivers control signals to a triac which controls the current supplied by a step-down transformer to the infrared lamp. The microcontroller also receives a dwell time adjustment signal which controls the length of the pulses of the infrared lamp. The microcontroller also controls a lamp-on indicator LED and a digital read out lamp which indicates the length of the light pulses. Advantageously, a feedback circuit is also provided which includes a photo-diode that delivers a signal proportional to the intensity of the infrared lamp to an operational amplifier. The op-amp delivers the signal to an analog-to-digital converter which supplies a converted signal to the microcontroller which, in turn, controls the triac accordingly in response to the intensity detected.

The infrared coagulator apparatus of the invention causes thermal coagulation by elevating the tissue temperature to about 100° C. without smoke or odor. The apparatus may be used for coagulation of bleeding, such as at the donor sites of hair transplant plugs. The coagulator is also suitable for causing coagulation at a hemorrhoidal plexus to cause the plexus to shrink and recede. Additionally, the coagulator may be used to remove decorative tattoos, reduce swollen nose membranes caused by chronic rhinitis, dry up genital warts or to remove warts or other skin lesions.

Other features and advantages of the present invention will become apparent from the following description of the invention which refers to the accompanying drawings.

BRIEF DESCRIPTION OF THE DRAWINGS

The invention will now be described in greater detail in the following detailed description with the reference to the drawings in which:

FIG. 9A is a cross-sectional view of a disposable sheath and contact tip in accordance with the invention.

FIG. 9B is a sectional view of the sheath of FIG. 9A.

FIG. 9C is a sectional view of the contact tip of FIG. 9A.

FIG. 9D is a left side elevation view of FIG. 9C.

FIG. 9E is a sectional detail taken from FIG. 9C.

FIG. 12A is an elevation view of the left side hand grip.

FIG. 18 is an exploded top front perspective view of the IRC housing and control unit.

FIG. 18A is an exploded bottom rear perspective view of the assembly of FIG. 18.

FIG. 19 is a top front exploded perspective view of the assembly of FIG. 18 showing the component parts before they are assembled together.

FIG. 19A is a bottom front perspective view of the FIG. 19.

DETAILED DESCRIPTION OF THE PREFERRED EMBODIMENTS

Figure 1:
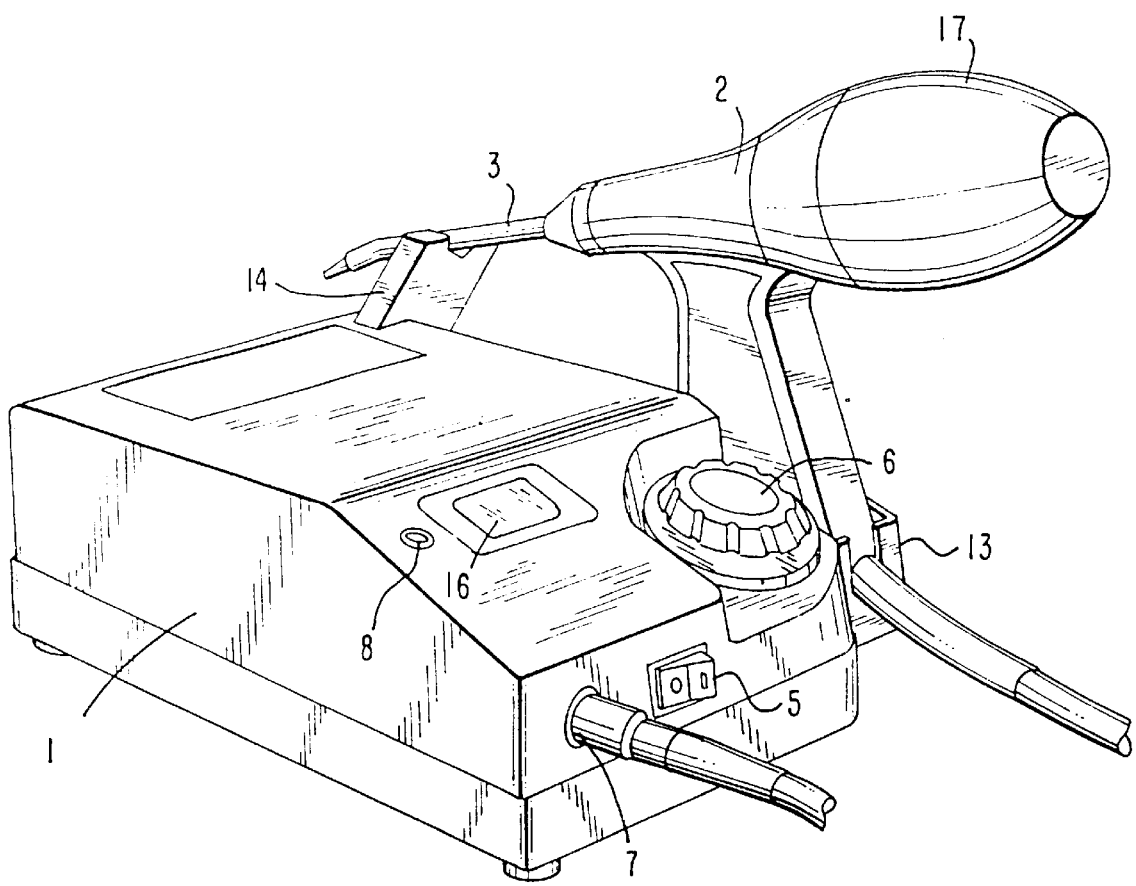
FIG. 1 shows a perspective view of an embodiment of the invention.
Figure 2:
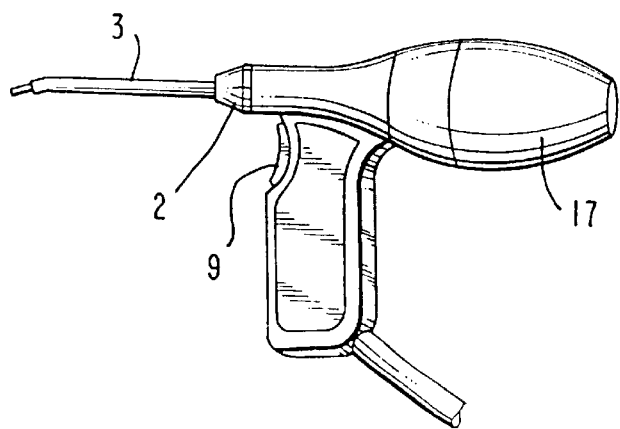
FIG. 2 shows a side view of the hand piece assembly of FIG. 1.
Figure 3:
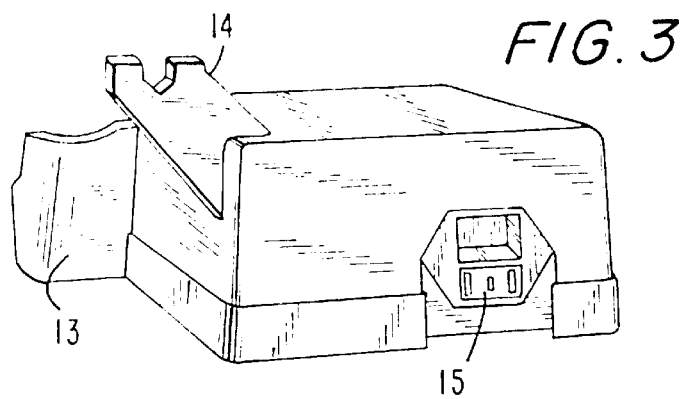
FIG. 3 shows a rear view of the console unit of FIG. 1.
Figure 4:
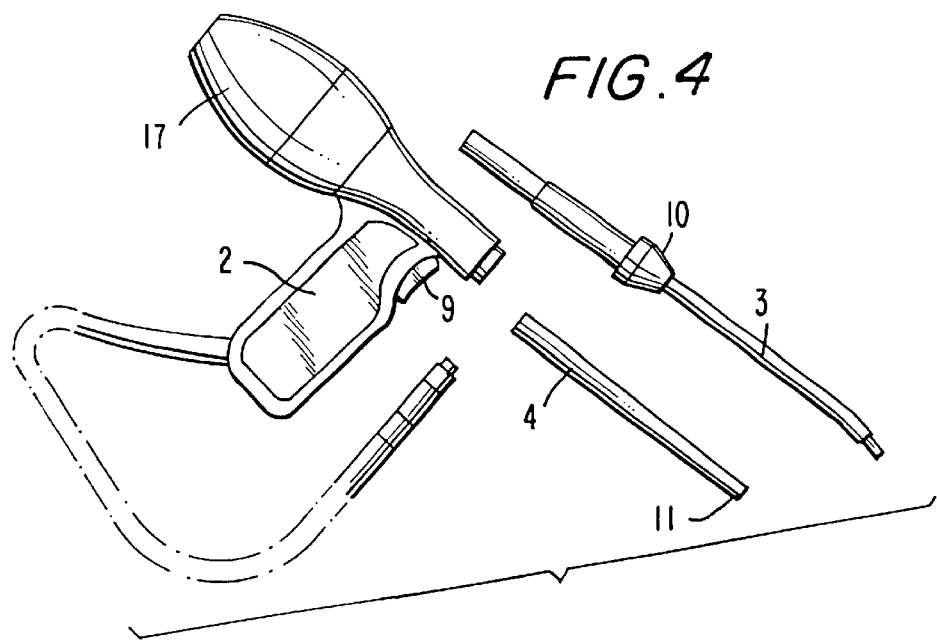
FIG. 4 shows an exploded view of the hand piece assembly of FIG. 2.

The present invention provides an infrared coagulation device that delivers short pulses of infrared and visible light from a light transmission source along a light guide to a small contact tip applicator that is applied directly to the target tissue. The transmitted light causes thermal coagulation that results in tissue necrosis. The depth of the coagulation is determined by the total amount of energy delivered which is controlled by adjusting the pulse duration.

Referring first to FIGS. 1–4, there is shown an embodiment of an infrared coagulator apparatus in accordance with the present invention. The coagulator includes a console unit 1, and a hand piece assembly 2. An on/off switch 5 is located at the front of the console unit and controls the 120 volt AC power that is preferably supplied to the console unit. Also located on the front of the console unit is a pulse duration control knob 6 that is adjusted to control the length of the infrared light pulses which are displayed on a digital timer display 16. An activation indicator light 8 illuminates when the device is activated.

The hand piece assembly includes a removable light guide 3 and a disposable contact tip and sheath 4. The hand piece assembly is also connected to the console unit by a cable which is inserted into receptacle 7 of the console unit. The hand piece assembly includes a handle with an activation trigger 9 and an insert receptacle for the light guide 3.

Situated within the hand piece assembly is a tungsten-halogen lamp which serves as a light source. A gold plated reflector is positioned to reflect infrared energy generated by the lamp and maximize transmission into the light guide. Such an arrangement is shown, for example, in U.S. Pat. Nos. 4,233,493 and 4,539,987.

The light guide includes a shielded quartz rod that has a threaded locking nut 10 at its proximal end. The locking nut 10 secures the removable light guide within an insert receptacle located on the hand piece assembly.

The disposable contact tip 4 is a single use sterile device that is attached to the distal end of the light guide by a user prior to each procedure. Typically, the disposable contact tip includes a 6 mm or 3 mm diameter optical window 16 that is placed in direct contact with the tissue and through which the infrared light radiation passes. Also included is a barrier sheath that protects the light guide 3 from contamination during use. Preferably, the disposable contact tips are supplied ETO sterile in individual packages.

The infrared coagulation apparatus of the invention generates timed pulses of light within a set range of from 0.5 to 3.0 second duration, preferably, with 0.1 second intervals between each pulse. The pulse duration is determined by the estimated depth of tissue necrosis required.

The apparatus is activated by depressing and holding the activation trigger 9 on the hand piece assembly to activate the lamp. Also activated is a digital timer 16 that will deactivate the lamp after a predetermined time interval based on the preset pulse duration selected. The activation indicator light 8 located on the top of the console unit 1 illuminates when the tungsten-halogen lamp is activated indicating that the tissue is being irradiated with infrared energy. A plastic part located at the rear of the hand piece assembly also glows to indicate that the lamp is on.

Figure 5A:
FIGS. 5A–5E illustrate an example of the preparation of the light guide in accordance with an aspect of the invention.
Figure 5B:
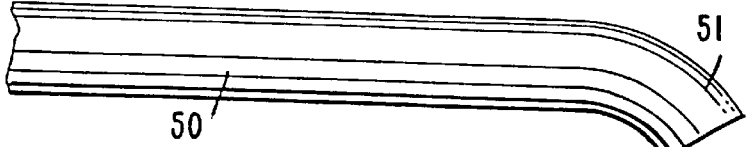
Figure 5C:
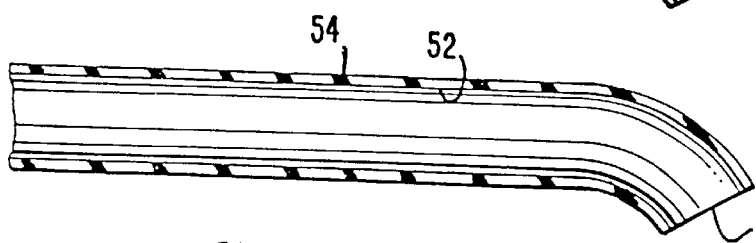
Figure 5D:
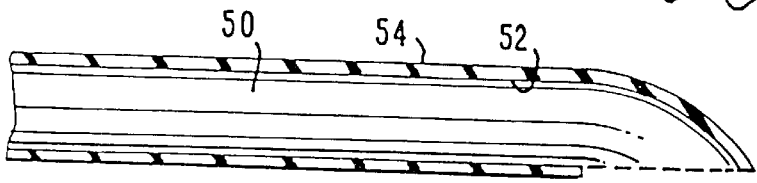
Figure 5E:
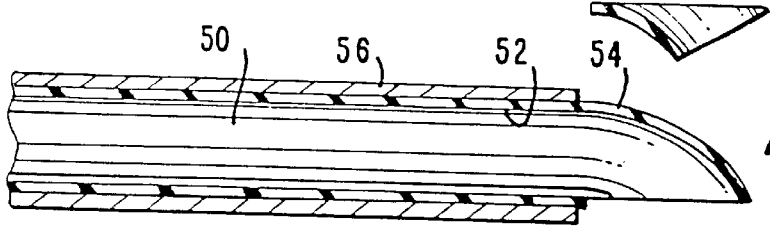

FIGS. 5A–5E illustrate an example of a process for preparing a quartz glass light guide in accordance with the invention. An initially straight, cylindrical section of quartz 50, shown in FIG. 5A, having a diameter of preferably 3.5 mm is heated and bent to have a 30° bend 51, for example, shown in FIG. 5B. A reflective coating 52 and a neoprene cladding 54 are then successively deposited on the outer wall of the quartz, as FIG. 5C shows. Then, as shown in FIG. 5D, a section of the quartz is removed, the cut surface is polished, as FIG. 5E shows, and a support cladding 56 is formed around the straight portion of the light guide.

Advantageously, the combination of the bend in the light guide and the reflective coating allows the transmitted light to exit the bent end of the light guide at angles up to about a 90° with respect to the axis of a cylinder.

Figure 6:
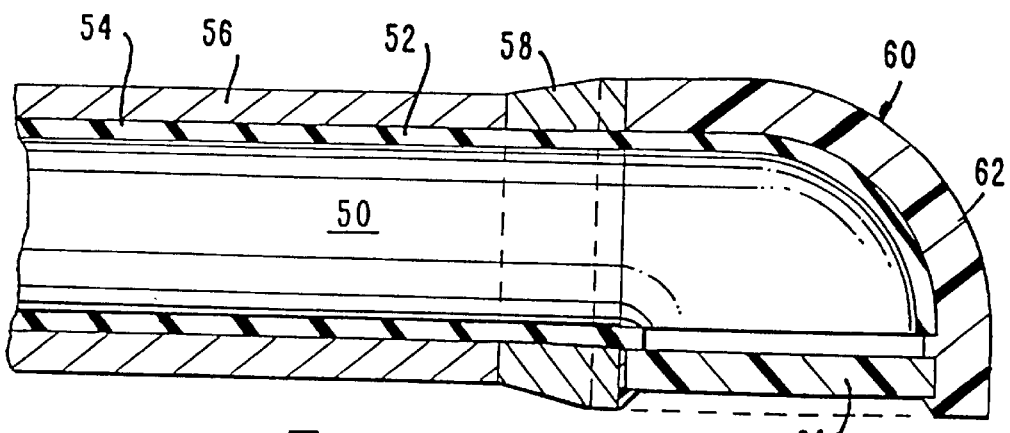
FIG. 6 shows a cross-sectional view of the light guide of FIG. 5 with an embodiment of a disposable contact tip of the invention.

Thereafter, an aluminum end cap 58 is epoxied onto the end of the support cladding adjacent to the bent portion of the light guide, shown in FIG. 6.

Alternatively, a straight quartz rod serves as the light guide and is covered with the reflective coating along the walls and at the distal end. A portion of the wall near the distal end is left uncoated so that the light exits at an angle substantially perpendicular to the axis of the rod.

FIG. 6 also shows an embodiment of a disposable contact tip 60 that fits over the bent end of the light guide. The disposable contact tip includes a substantially hemispherical plastic cap 62 which is preferably polyethylene and which securely fits into the aluminum end cap 58. A Teflon or PVC plate optical window 64 is secured to the plastic cap. The light is transmitted through the optical window 64 which directly contacts the tissue that is to be exposed to by the light.

Figure 7A:
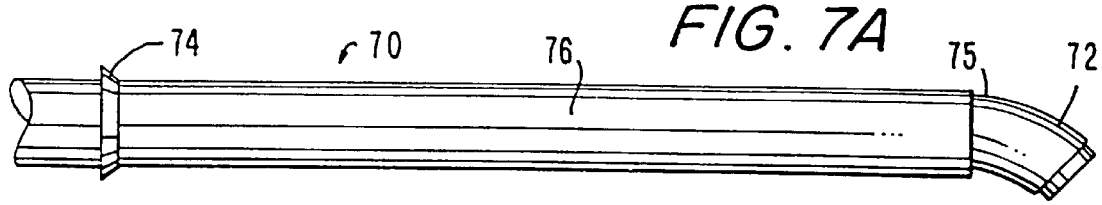
FIG. 7. shows another embodiment of a disposable contact- tip and sheath of the invention.
Figure 7B:
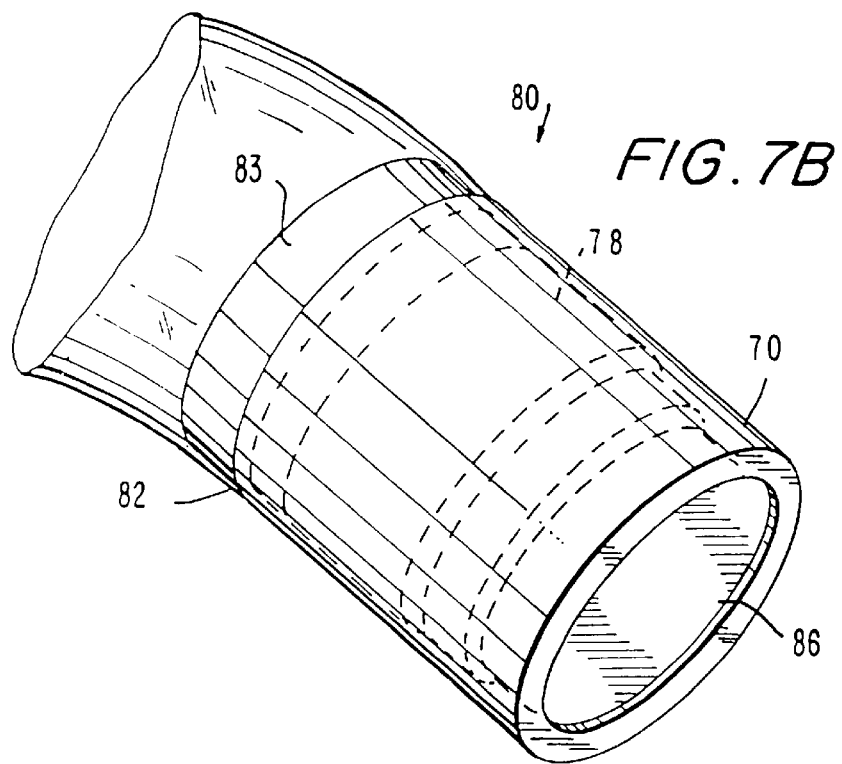
Figure 7C:
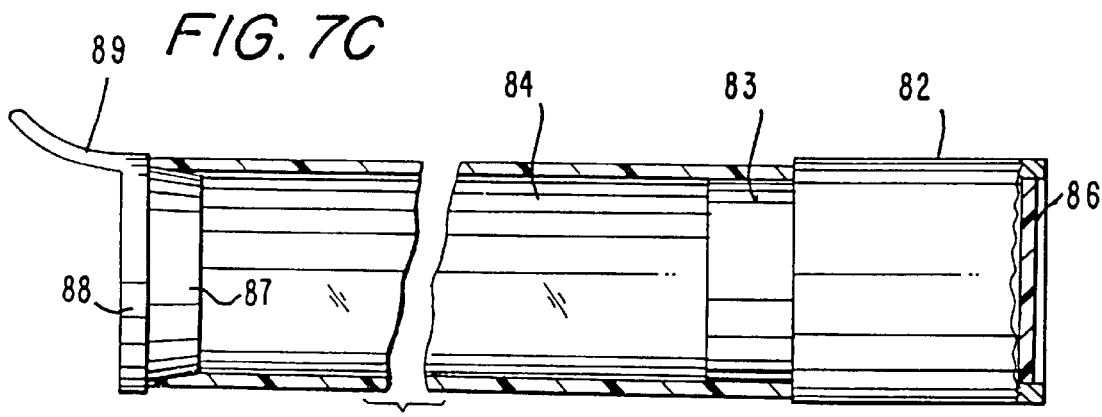

FIG. 7 illustrates another embodiment of a disposable contact tip and sheath according to the invention. Here, the contact tip and sheath are suitable for protecting a light guide structure having no bend or a slight bend at the distal end. The cylindrical light guide 70 includes a straight portion that is covered with support cladding and includes a retaining collar 74 near the proximal end of the light guide. A bent portion 75 may be incorporated into the distal end. The bent portion is coated with reflective coating 72 but is without cladding. The bend causes the light exiting at an oblique angle with respect to the axis of the cylindrical light guide that is substantially less than 90°. An aluminum end cap 78 is permanently attached to the end of the cladding at the distal end of the light guide.

In accordance with the invention, a disposable contact tip and sheath includes a body section 82 and sheath 84. The body section is a hollow cylindrical shape and fits over the end cap 78. A Teflon or PVC optical window 86 is held in place at one end of body portion 82 and contacts and protects the distal-end of the quartz light guide 70. At the opposing end of the body portion 82 is a step-down section 83 which is concentrically arranged with the body portion but has a smaller outer diameter and securely fits into end cap 78. The distal end of the plastic sheath 84 fits over the step-down section 83. Located at the proximal end of sheath 84 is a retainer ring 88 which includes another step-down section 87. When the sheath is slid over the light guide, cladding 72, the retaining ring 88 and step-down section 87 slide over retaining collar 74 and secure the sheath to prevent unintentional or accidental removal.

Figure 8:
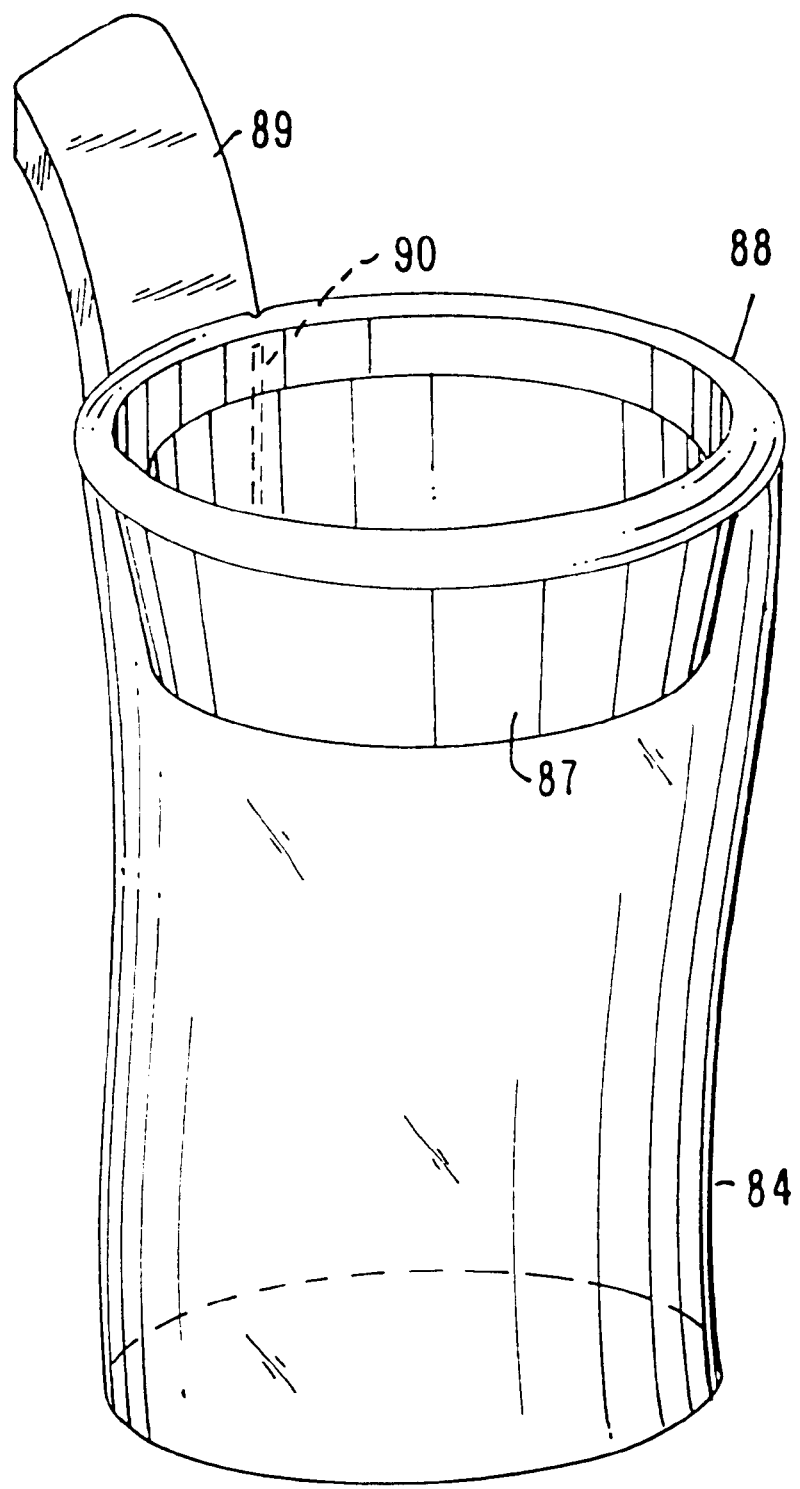
FIG. 8 shows a portion of the contact tip and sheath of FIG. 7 in greater detail.

In further accordance with the invention, FIG. 8 shows a pull tab 89 which is attached to ring 88 to facilitate removal of the sheath and contact tip 80 after its use. The sheath is removed by pulling on the tab 89 which causes the ring to tear at a weakened notch 90 and thus permits the sheath to tear along its length and be freed from the light guide. Advantageously, the sheath is damaged during its removal so that it is no longer suitable for reuse. Thus, a non-sterile, used sheath, cannot be reapplied over the light guide.

Preferably, two injection molded plastic parts serve as the body section 82 and the retainer ring 88, respectively, and are all heat-treated together with a Teflon disc and a tubular sheath to seal the components into one unit.

FIGS. 9A–9E show example views of another embodiment of the disposable sheath and contact tip in accordance with the invention. FIG. 9A shows the assembly 91 comprising a disposable sheath 92 and attached contact tip 93. These components are further shown in greater detail in FIGS. 9B–9E, where contact tip 93 has a proximal end 94 for insertion into the distal end 95 of the sheath 92 where it is sealed. This sheath is made of Unichem 18575 SF which is detailed in Appendix B attached hereto. The contact tip 93 is made of Georgia Gulf CL-7049 vinyl compound which is detailed in Appendix C attached hereto. In an alternative construction of the disposable sheath and contact tip, a single plastic or other compound is used for making the entire component as a single element, with the contact tip being generally stiff, particularly including the distal end light transmissive window 96 and the sheath part 92 being generally flexible sheet material.

Figure 10:
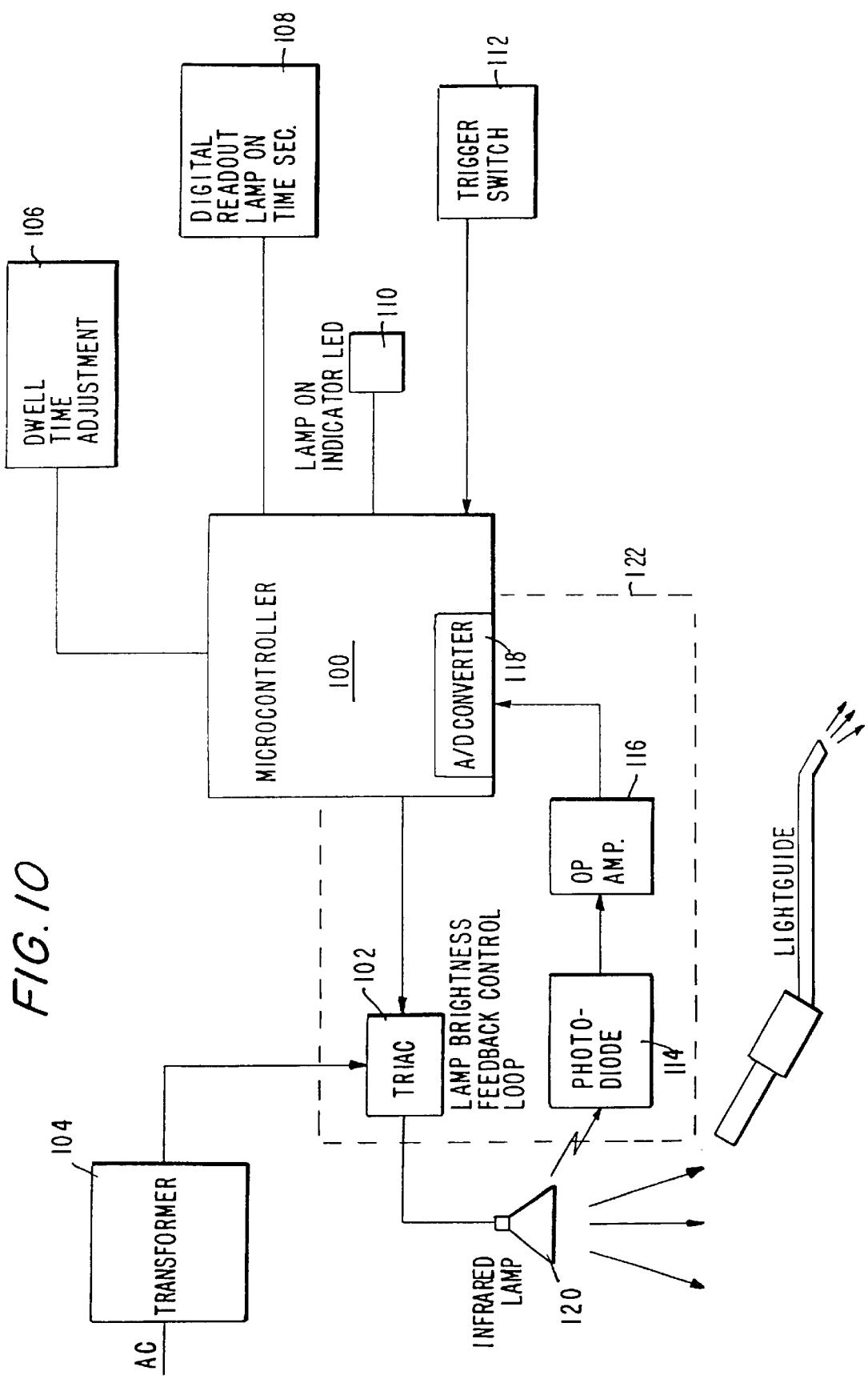
FIG. 10 is block diagram showing an embodiment of the power supply and control circuit of the invention.

FIG. 10 shows a block diagram of an embodiment of a power supply and control circuit for controlling the infrared coagulator apparatus of the invention. A step-down transformer 104 is supplied with 120 volts AC and delivers a 19.5 volt, 8 amp supply power to triac 102 which, in turn, controls the current supplied to the infrared lamp 120 in response to a control signal supplied by a microcontroller 100. The control signals delivered by the microcontroller 100 control the length of the light pulses generated by the lamp 120 in response to a signal supplied by dwell time adjustment 106. The microcontroller also displays the length of the pulses on digital read out lamp 108. The microcontroller also controls lamp on indicator LED 110 to indicate that the lamp is turned on.

Also included is a lamp brightness feedback control loop 122 which includes a photo-diode detector 114 that delivers a signal to operational amplifier 116 as a function of the brightness of infrared 120. The op-amp 116 then delivers an amplified signal to an analog-to-digital converter 118 which in turn supplies a digital signal to microcontroller 100. The microcontroller thus, controls track 102 to vary the current supplied to the lamp 120 until the detected brightness reaches a desired predefined level.

Figure 11:
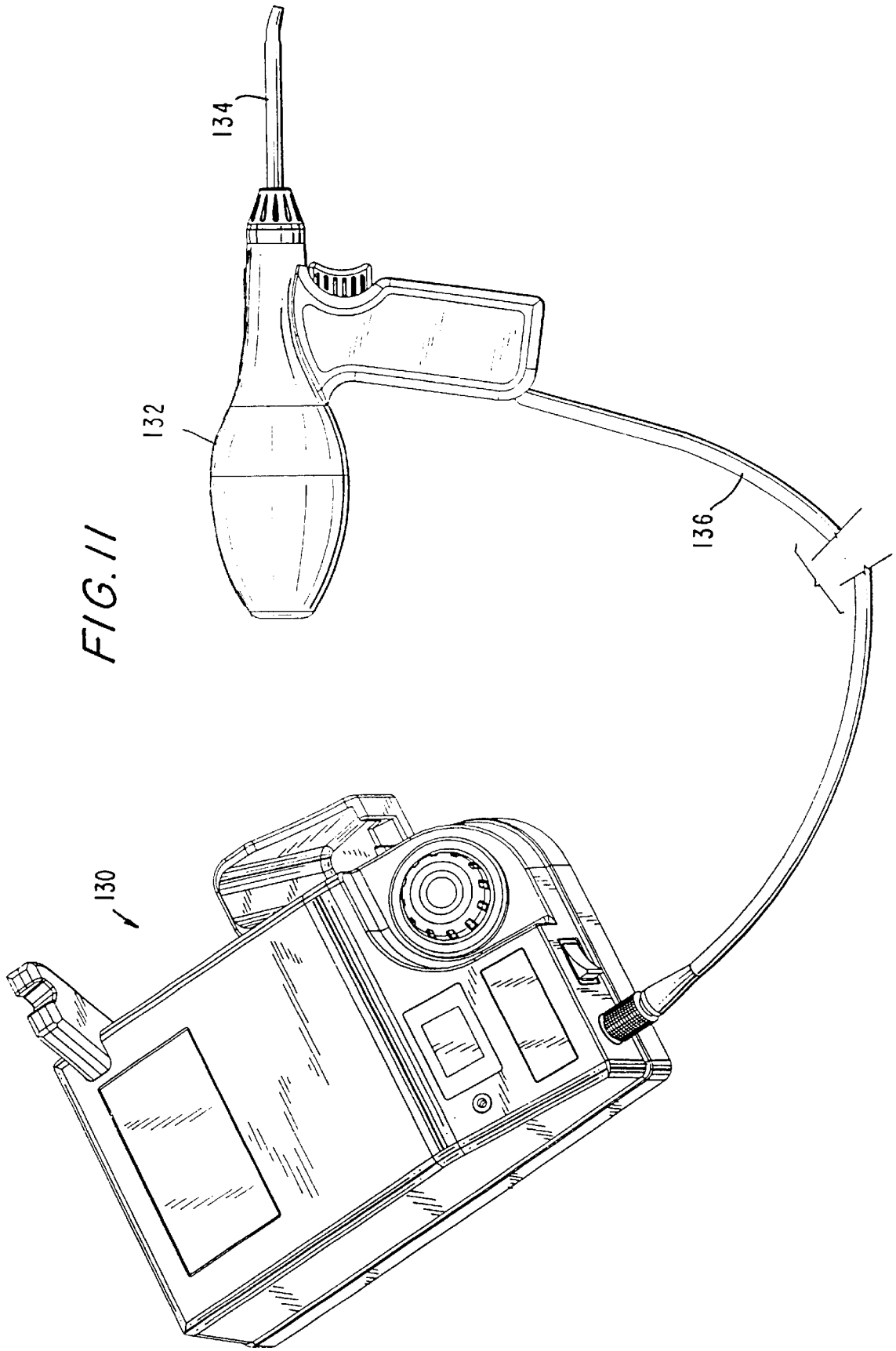
FIG. 11 is top perspective view of the IRC assembly comprising the base housing and control unit on the left, the light guide and handle assembly on the right, and the connecting cable.

FIG. 11 illustrates the IRC assembly consisting of the housing and control unit 130 and the handle assembly and light guide 132, 134 connected to the control unit by cable 136, which principal components will be described in much greater details as follows.

Figure 12:
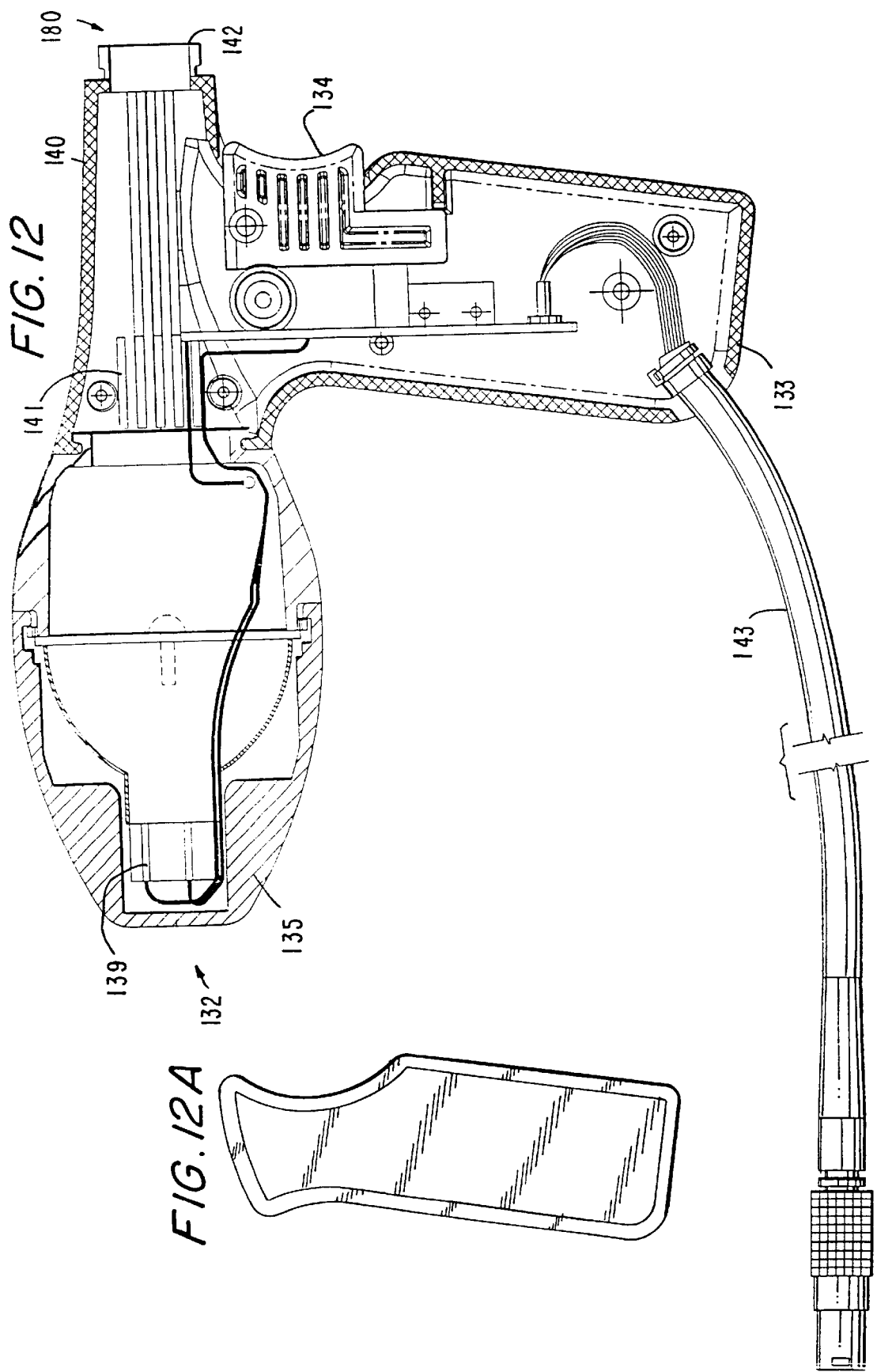
FIG. 12 is a sectional elevation view of the handle portion of the light guide.

FIG. 12 shows the detailed construction of the hand piece assembly 132 which includes a handle 133 and a trigger 134, and a light housing 135 formed as rear cup 136 and funnel 137 which are joined together and contain a light source 138 which is a 20 watt parabolic Osram lamp mounted in socket 139 at the rear of cup 136. Funnel 137 is a tapered partial cylindrical section 140 which receives the proximal end of the light guide as explained later. Within housing 140 guide ribs 141 to receive said proximal end of the light guide and position and center and support same. At the forward or front end of the hand piece is a male thread section 142 which eventually receives the lock nut 166 which is on the light guide and thereby secures light guide to the hand piece. The various components of this hand piece, namely the rear cup 136, the funnel 137, the front housing 140 are all of typical molded plastic known in the industry such as ABS polycarbonate, which is strong and heat resistant.

The lamp shown is a tungsten-halogen lamp which delivers visible and infrared radiation focused generally conically to a spot at the proximal end surface of said quartz rod.

Within this hand piece is trigger 134 which when activated closes the circuit of the system conducted through cable 143 to the control unit 130 described earlier.

FIG. 12A illustrates the left hand grip molded plate which covers the handle portion. A mirror image element covers the right side, the clamp shell-like elements enclosing the hand piece and trigger unit.

Figure 13:
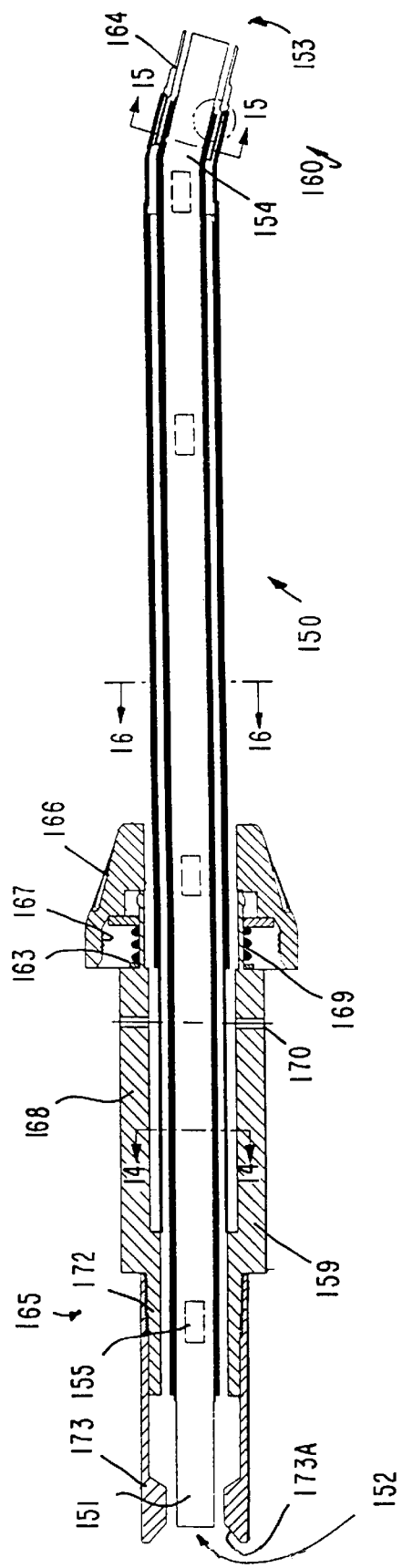
FIG. 13 is a sectional elevation view of one embodiment of the light guide assembly.
Figure 13A:
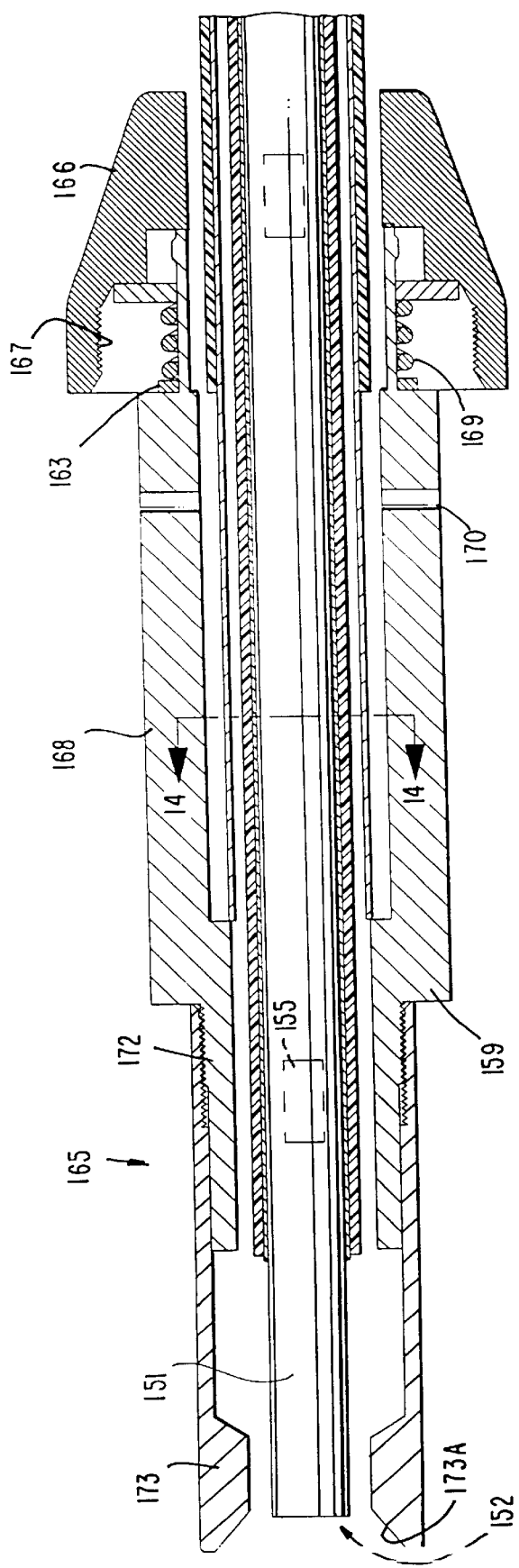
Figure 13B:
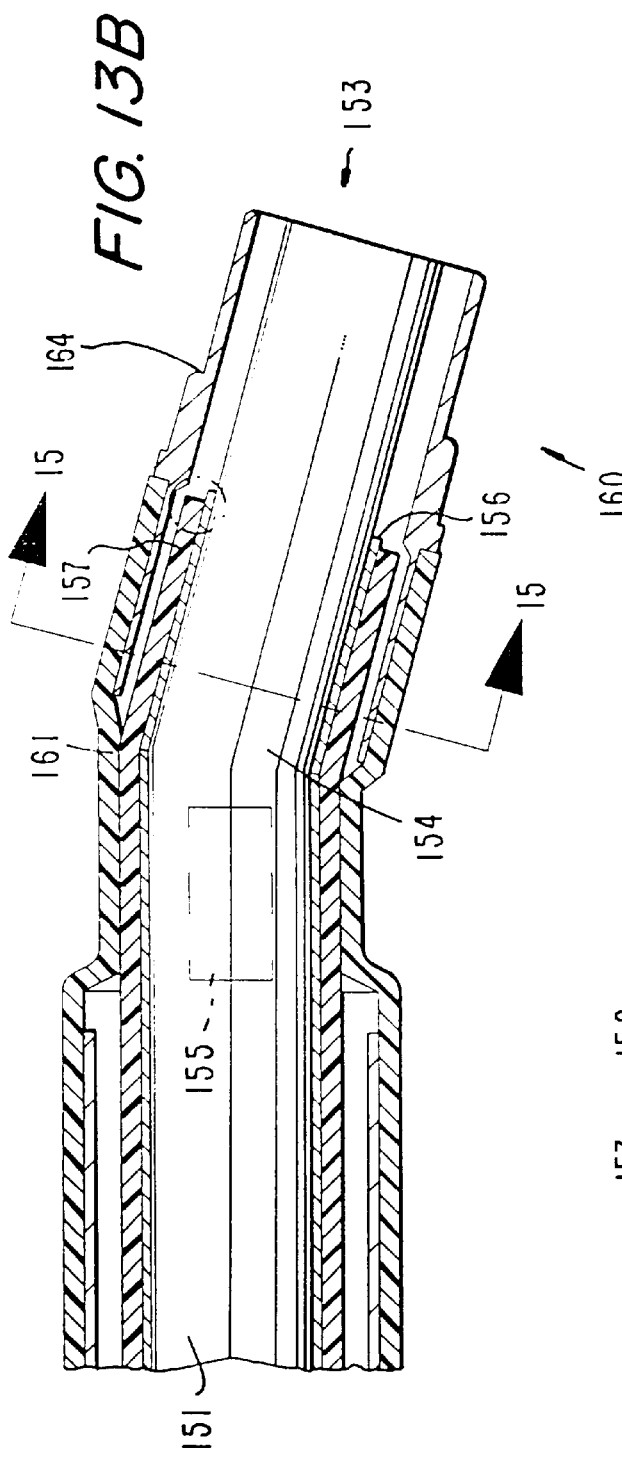

FIG. 13 illustrates the light guide assembly 150 for the embodiment where the central quartz rod 151 has dimensions of 6 mm diameter by 120 mm in length. In this light guide assembly the central quartz rod 151 has a proximal end 152 and a distal end 153, the latter being bent at area 154 to an approximate 15° angle. As further explained in FIGS. 14, 15, 16 and 17 which are sectional views through FIG. 13, this light guide assembly 150 is formed of said quartz rod 151 covered by a sheet of aluminum foil of typical heavy duty Reynolds® wrap as is readily obtainable in grocery or hardware stores. This foil is a single sheet wrapped around the quartz rod until about one inch overlies the other and is secured thereto by small pieces of Mylar® tape 155. Four such pieces of tape are shown axially spaced along the length of the foil covering the quartz rod.

Figure 17:
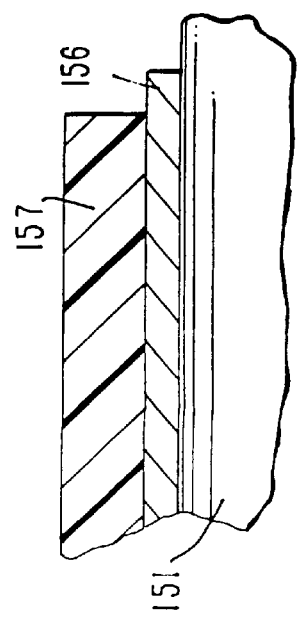
FIG. 17 is a fragmentary detailed view enlarged and taken at point A in FIG. 13.

Radially outward of the foil is an inner layer of shrink tubing made of Teflon® which is positioned to extend along the length of the quartz rod radially outward of the foil and covering same. The foil 156 is thus covered by inner tube shrink layer 157 which initially is oversized in diameter and is easily positioned to surround and enclose the foil layer until it is heated and shrunk to fit snugly thereon and protect it. The shiny highly reflective side of foil 156 is placed against the outer surface of the quartz rod, and as seen in FIG. 17, the foil 156 extends about $1/32^{nd}$ of an inch farther along the length of the quartz rod than the shrink tubing so that the light reflected within the quartz rod strikes the foil at all relevant places and is not allowed to escape and strike the shrink tubing which would absorb the light.

Figure 15:
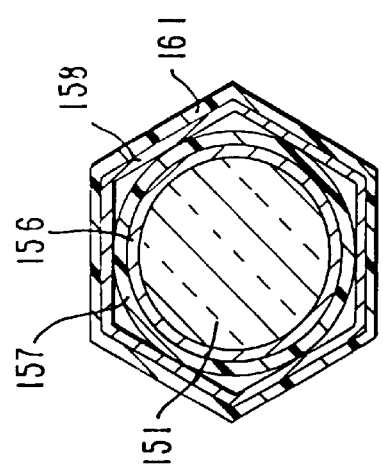
FIG. 15 is a sectional line taken along line C—C of FIG. 13.
Figure 14:
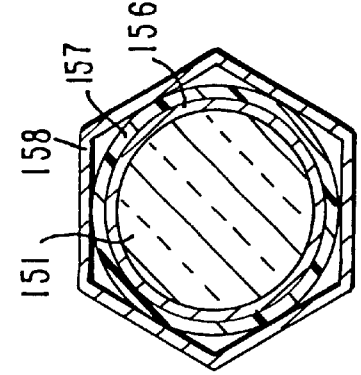
FIG. 14 is a sectional view taken along line B—B of FIG. 13.
Figure 16:
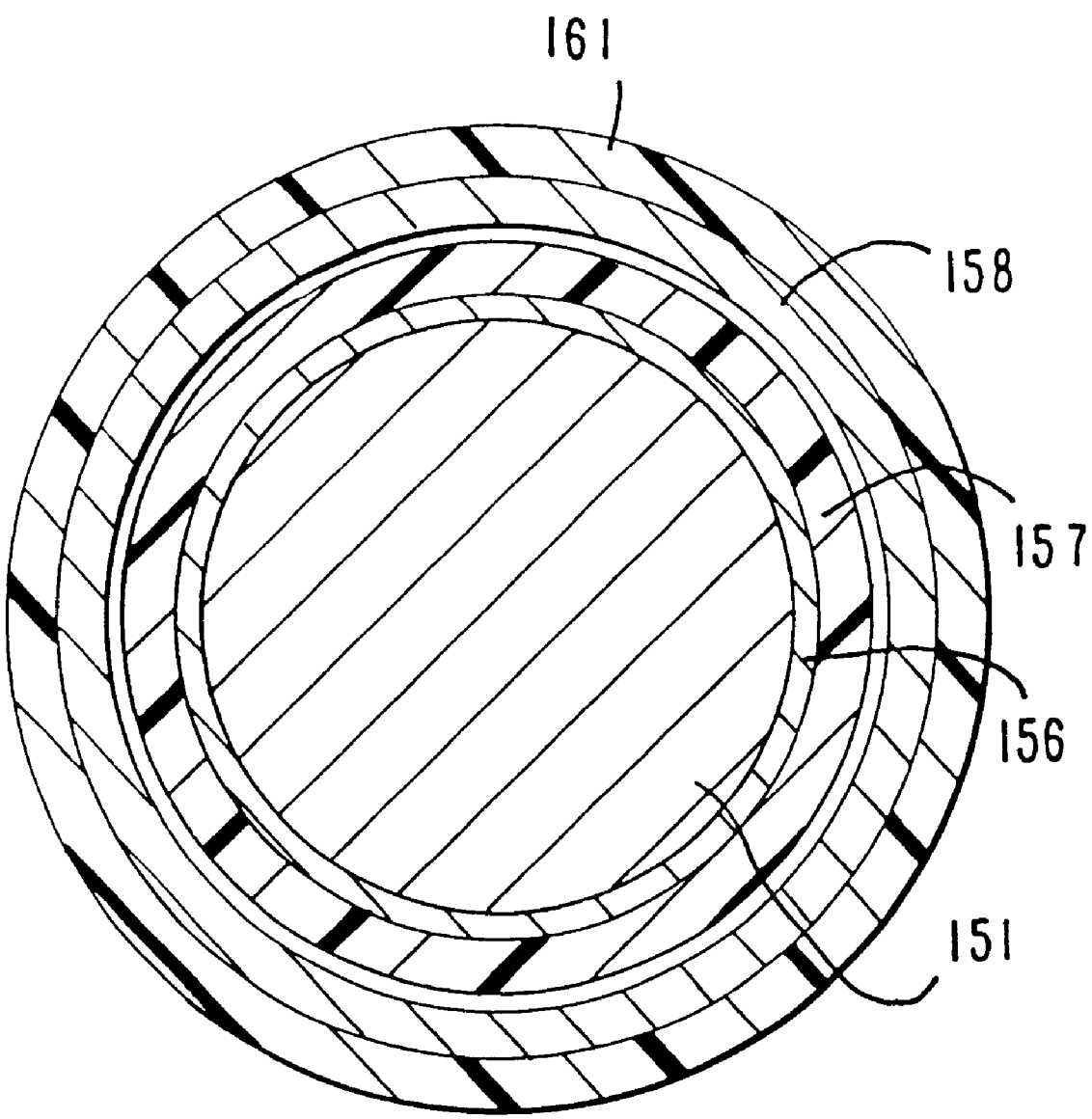
FIG. 16 is a sectional view taken along line D—D of FIG. 13.

Radially outside of the inner tube 157 is yet another sleeve or tube 158 made of brass which fits about shrink tube 157 and extends along most of its length. However, as seen in FIG. 13, support sleeve 158 extends from position 159 near the proximal end forward to position 160 near the distal end. In the vicinity of 159 and Sectional Line B—B, the support sleeve is crimped along a length approximately 1 ¼ inches into a hexagonal shape as seen in FIGS. 14 and 15 where it resides snugly against the inner shrink tube layer. The support sleeve is similarly crimped in the area of Section Line C—C. In the area of Section Line D—D between B—B and C—C the support tube remains essentially round and uncrimped.

Radially outward of this support sleeve is yet another Teflon® shrink tube layer 161 which extends most of the length of the assembly from point 162 at the distal end back to point 163 somewhat near the mid-length.

The distal end 153 of the light guide as seen in FIG. 13 directs the light radiation outward at an angle of about 15 degrees. As discussed earlier, this angle may vary, and also, this distal end may be modified to be essentially side-looking by rounding or otherwise shaping its terminal end surface and cladding said surface with highly reflective material such as aluminum foil, and leaving a transverse-directed window in the foil for directing the output light radiation transversely of the light propagation direction along the main length of the quartz rod.

FIGS. 5B and 5C show one embodiment of a quartz rod with a bent distal end. If nothing more was done, the light emission direction would be essentially outward in the direction of the bent end.

FIGS. 5D, 5E and 6 show the quartz rod of FIG. 5C with its distal end cut to provide a transverse light exit surface. Preferably, this exit surface would define a side-looking window of predefined area, with the remainder of this distal end clad with highly reflective aluminum foil. In a still further embodiment the quartz or other suitable rod would be generally straight along its length, which length and distal end are clad with said foil except for a side-looking window.

There is a connection assembly 165 positioned at the generally proximal end of the light guide assembly. This consists of locknut 166 having internal threads 167, and housing 168 which has a forward extending sleeve 169 that engages the locknut, and a threaded aperture 170 for receiving set screw 171 not shown, and has a rear portion 172 with external threads for receiving funnel 173 screwed thereon. The funnel has proximal end 173A which helps guide light from the lamp to the proximal end of the quartz rod. The outer diameter of the funnel engages ribs 141 in the hand piece as described below.

In this sub-assembly the set screw 171 which extends through aperture 170 continues radially inward until it engages a flat surface 174 seen in FIG. 14 which securely couples this housing to the support sleeve 158 about the quartz rod.

In subsequent assembly of said light guide 150 and said handle and hand piece 132, the proximal end of the light guide assembly, namely the funnel 173 is extended into aperture 180 (see FIG. 12) at the front end of the hand piece until it reaches ribs 141 which guide, center, position and stop it. The internal threads 167 of the locknut 166 are screwed onto the male threads 142 at the front end of the hand piece, and this securely locks the light guide assembly to the hand piece assembly.

Returning to FIG. 13 and the distal end of the light guide, the quartz rod has aluminum foil with the shiny reflective side facing radially inward against the quartz rod along the bent area as further shown in FIG. 15. Radially outward of this foil is the inner shrink tube which again extends less in length than the foil so that the light is reflected off the foil and cannot reach the shrink tube. At the tip or distal end of this assembly is secured an aluminum ferrule 164 or tube extending until its opening is flush with the end of the quartz rod. The terminal end of the ferrule sleeve has a reduced outer diameter for receiving a disposable sheath of the type generally disclosed above with reference to FIGS. 7–9. The removable and disposable sheath allows this IR coagulator instrument to remain uncontaminated even though it is used on a succession of patients. The cylindrical cap of aluminum or other rigid material at the distal end of the sheath secures the light transmissive window at the terminal end thereof and provides a stable coupling with the distal end of the light guide. Since the sheath material comprises this flexible plastic sheet material, it can easily be slid onto a light guide even if there is a bend at the distal end. The sheath may be made from a variety of plastic materials or latex rubber.

The locknut 166 is made of molded ABS polycarbonate plastic, the housing 168 is made of a plastic called ULTEM® having an outer diameter of about 0.590 inches; the funnel 173 is made of aluminum and has an outer diameter of 0.55 inches; the ferrule 164 at the distal end of the light guide has a 0.274 outer diameter as it surrounds the quartz rod of 6 mm diameter.

FIGS. 18, 18A shows the base unit 190 including therein the IRC control power supply and control sub-assembly. There is outer housing 191, timer control knob 192, digital time display window 193, power on/or switch 194, on/or light indicator 195. Also in FIG. 18, beneath the housing 191 is the chassis 192 which includes sub-housing 193 to receive and hold the handle of the hand guide or hand piece sub-assembly.

Figure 20A:
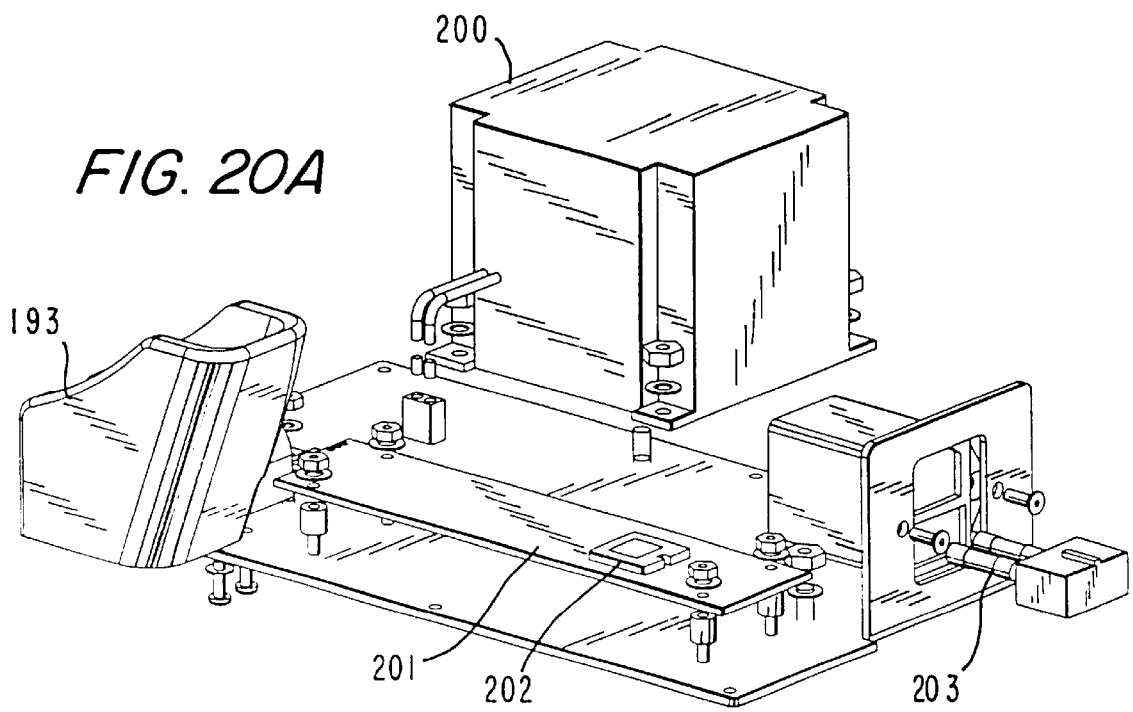
FIG. 20A is an exploded top rear perspective view of FIG. 20.
Figure 20:
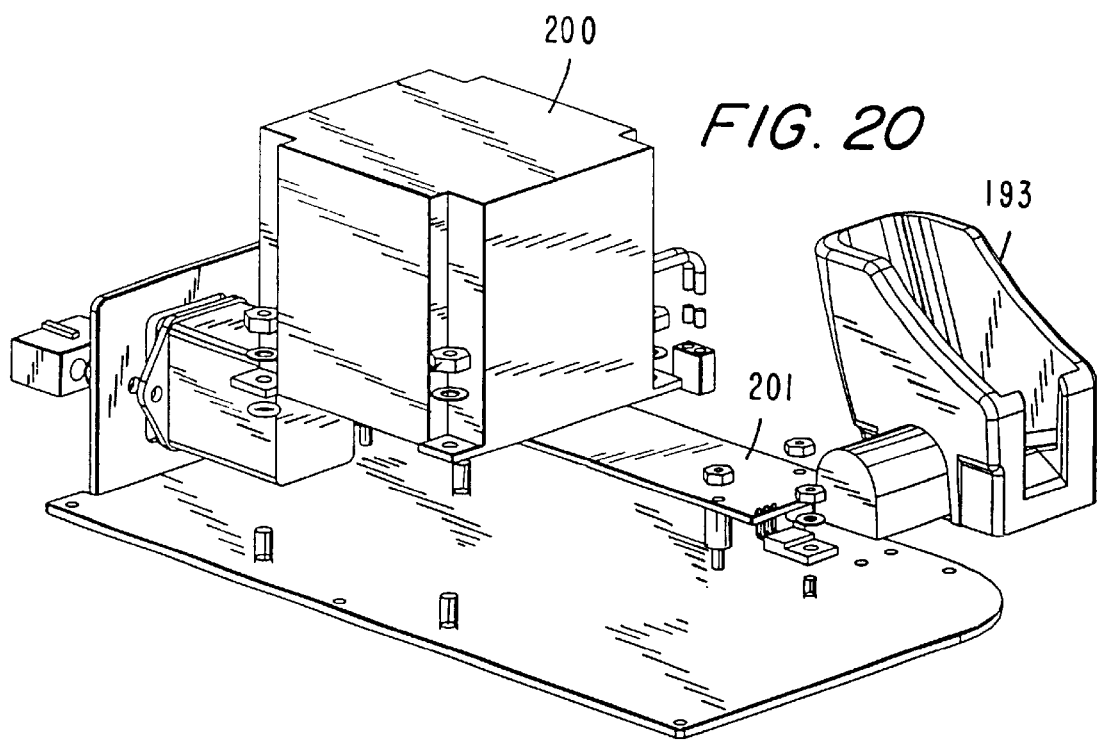
FIG. 20 is an exploded top front perspective view of the IRC chasse which is situated within the housing and control unit of FIGS. 18 and 19.

FIGS. 19, 19A show the housing and control unit of FIGS. 18 and 18A before they are assembled so that control knob 192 is shown in exploded position above the housing 191 and the power switch 194 as shown before it is moved inward to its final position. The same is true of the LED Lens 195 showing the on/off condition of the unit. Also, there is a DIN connection 196 in FIG. 19. FIGS. 20 and 20A show the chassis and inner components which fit within the control housing of FIGS. 18 and 19. These components include the transformer 200, the PCB (printed circuit board) control board 201 and the programmed chip 202. Another minor component as shown in FIG. 20A is the low blow fuse 203. The circuit diagram of FIG. 10 discussed above discloses the overall circuit of this apparatus and is applicable to the apparatus of FIGS. 12–20.

A copy of an Operating and Reference Manual for the embodiment of FIGS. 11–20 of the new Infrared Coagulation apparatus is attached hereto as Appendix D.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An apparatus for applying light radiation to shrink hemorrhoids in a human patient, said apparatus comprising:

a source of light radiation which is not a laser, comprising infrared radiation;

a light guide having a proximal end optically coupled to said source of light radiation and a distal end with a light radiation emitting end surface;

a power supply which supplies power to said light radiation source;

a photo light energy detector disposed within said apparatus so as to receive energy output emitted from said light radiation source, said photo light energy detector producing an output in response to said received energy output; and a controller coupled to said photo light energy detector and said light radiation source, wherein said controller receives said output from said photo light energy detector and controls said source of light radiation to produce a predetermined light radiation intensity in response to said output.

2. The apparatus as claimed in claim 1, wherein said controller controls said light source through a triac.

3. The apparatus as claimed in claim 1, further comprising:

a timer coupled to said controller wherein said controller controls said light radiation source to produce said predetermined light radiation during a time period dictated by said timer, and wherein said controller turns off said light radiation source after the expiration of said time period.

4. The apparatus as claimed in claim 3, further comprising a timer indicator which indicates how long said light source has emitted said light.

5. An apparatus according to claim 1, wherein said light guide comprises a quartz rod.

6. An apparatus according to claim 5, wherein said quartz rod has an outside diameter in the range of 3 to 6 mm and length in the range of 90 to 210 mm.

7. An apparatus according to claim 5, wherein said light guide further comprises a rigid tubular housing in which said quartz rod is situated and secured.

8. An apparatus according to claim 7, wherein said tubular housing comprises a first tube of aluminum sheet material closely surrounding said quartz rod, said sheet material having a highly reflective surface facing the outer surface of said quartz rod.

9. An apparatus according to claim 8, wherein said tubular housing further comprises a second tube of plastic or rubber closely surrounding said first tube, a third tube of rigid metal closely surrounding said second tube, and a fourth tube of plastic or rubber closely surrounding said third tube.

10. Apparatus according to claim 9, wherein said second and fourth tubes comprise flexible Teflon®.

11. Apparatus according to claim 8, wherein said first tube extends generally the full length of said quartz rod.

12. An apparatus for applying light radiation to shrink and not cut hemorrhoids in human patients by said apparatus comprising:

an infrared light radiation source which is not a laser, a rigid light guide having a first end optically coupled to said light radiation source and a distal end with a light emitting end surface, said light radiation source propagating light in a generally axial propagation direction along and within said light guide, and a disposable contact tip for covering said distal end of said light guide, said disposable contact tip comprising:
  a) a generally rigid cap including a window of Infrared light transmissive material, said cap shaped and dimensioned to cover the distal end of said light guide, and
  b) a flexible sheath extending axially and integrally from said cap, said sheath configured to extend from said cap axially inward along said light guide.

13. Apparatus according to claim 12, wherein said distal end has a terminal surface portion situated transverse of said generally axial propagation direction, whereby light transmitted internally within said quartz rod is reflected by said terminal surface portion in a direction transverse of said propagation direction.

14. Apparatus according to claim 13, wherein said terminal surface portion reflects said light at an angle generally 90 degrees from said propagation direction.

15. Apparatus according to claim 13, wherein said terminal surface is curved and defines a concave inner wall surface.

16. An apparatus for applying light radiation to shrink and not cut hemorrhoids in a human patent said apparatus comprising:

an infrared light radiation source which is not a laser, a rigid light guide having a proximal end optically coupled to said light radiation source and a light emitting distal end a power supply which supplies power to said light radiation source and a disposable contact tip for covering said distal end of said light guide, said disposable contact tip comprising:
   a) a generally rigid cap including a window of infrared light transmissive material, said cap shaped and dimensioned to cover the distal end of said light guide, and
   b) a flexible sheath extending axially and integrally from said cap, said sheath configured to extend from said cap axially inward along said light guide.

17. Apparatus according to claim 16, wherein said sheath comprises flexible water impervious sheet material and said window comprises a rigid highly light transmissive material.

18. Apparatus according to claim 16, wherein said window comprises a Teflon® plate.

19. Apparatus according to claim 18, wherein said sheath comprises a closed end which includes said window and an open end defined by a peripheral edge, said peripheral edge including a tab which when pulled tears a longitudinal strip along the length of said sheath to facilitate removal of said sheath from said light guide.

20. An apparatus for applying light radiation to shrink and not cut hemorrhoids in human patients, said apparatus comprising:

an infrared light radiation source which is not a laser;

a rigid light guide having a proximal end optically coupled to said light radiation source and a distal end with a light radiation emitting end surface;

a power supply which supplies power to said light radiation source;

said light radiation source propagating light in a generally axial propagation direction along and within said light guide, wherein said distal end directs light to exit said light guide in a direction transverse to said generally axial propagation direction, and a disposable contact tip for covering said distal end of said light guide, said disposable contact tip comprising:
   a) a generally rigid cap including a window of infrared light transmissive material, said cap shaped and dimensioned to cover the distal end of said light guide, and
   b) a flexible sheath extending axially and integrally from said cap, said sheath configured to extend from said cap axially inward along said light guide.

* * * * *